US008101665B2

(12) United States Patent
Masjedizadeh et al.

(10) Patent No.: US 8,101,665 B2
(45) Date of Patent: Jan. 24, 2012

(54) PROCESS FOR SYNTHESIS OF TRITIATED AND DEUTERATED THIORPHAN AND ACETORPHAN

(75) Inventors: Mohammand R. Masjedizadeh, San Jose, CA (US); Shao-Yong Wu, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 726 days.

(21) Appl. No.: 12/316,946

(22) Filed: Dec. 17, 2008

(65) Prior Publication Data
US 2011/0319656 A1    Dec. 29, 2011

Related U.S. Application Data

(60) Provisional application No. 61/014,120, filed on Dec. 17, 2007.

(51) Int. Cl.
| A01N 31/18 | (2006.01) |
| A01N 31/00 | (2006.01) |
| A61K 31/165 | (2006.01) |
| A61K 31/095 | (2006.01) |
| C07C 321/00 | (2006.01) |
| C07C 323/00 | (2006.01) |
| C07C 318/00 | (2006.01) |

(52) U.S. Cl. .................. 514/618; 514/706; 564/162
(58) Field of Classification Search .................. 514/618, 514/706; 564/162
See application file for complete search history.

(56) References Cited

U.S. PATENT DOCUMENTS
5,296,509 A    3/1994 Duhamel et al.

OTHER PUBLICATIONS

De la Baume, S., et. al. "Labelling and exploration of the active site of Enkephalinase )EC 3.4.24.11) in Kidney Membranes with [3H] thiorphan as ligand," European Journal of Pharmacology (1988) vol. 149, pp. 121-129.
De la Baume, S., et. al. "Evaluation of Enkephalinase Inhibition in the Living Mouse, Using [3H] Acetorhphan as a Probe," The Journal of Pharmacology and Experimental Therapeutics (1988) vol. 247 (2), pp. 653-660.
Fournie-Zaluski, M.C., et. al. "Study of Crucial Components in Enkephalinase Inhibitors and Synthesis of Photoaffinity Labels and Tritiated Derivatives," American Peptide Symposium XX (1981) vol. 7, pp. 425-428.
Huijghebaert, S., et. al. "Racecadotril Versus Loperamide; Antidiarrheal Research Revisited," Digestive Diseases and Sciences (2003) vol. 48 (2), pp. 239-250.
Lecomte, J., et. al. "Pharmacologist Properties of Acetorphan, a Parenterally Active "Enkephalinase" Inhibitor," The Journal of Pharmacology and Experimental Therapeutics (1985) vol. 237 (3), pp. 937-944.
Matheson, A. J., et. al. "Racecadotril," Drugs (2000) vol. 59 (4), pp. 829-835.
Pollard, H., et. al. "Characterisation of two probes for the localisation of enkephalinase in rate brain: [3H] thiorphan and 125I-labeled monoclonal antibody," European Journal of Pharmacology (1987) vol. 133, pp. 155-164.
Beight, D. W., et. al. "Synthesis of Contrained Thiorphan Analogs as Inhibitors of Neutral Endopeptidase1," Bioorganic & Medicinal Chemistry Letters (1996), vol. 6 (17), pp. 2053-2058.
Fournie-Zaluski, M.C., et. al. "1H NMR Configurational Correlation for Retro-Inverse Dipeptides: Application to the Determination of the Absolute Configuration of "Enkephalinase" Inhibitors. Relationships between Sterochemistry and Enzyme Recognition," Journal of Medicinal Chemistry (1986), vol. 29, pp. 751-757.
Senderoff, S.G., et. al. "Synthesis of the Enantiomers and Three Racemic Metabolites of Carvedilol Labeled to High Specific Activity with Tritium," Journal of labelled Compounds and Radiopharmaceuticals (1993) vol. XXXIII, No. 12, pp. 1092-1105.

*Primary Examiner* — Sreeni Padmanabhan
*Assistant Examiner* — Kendra D Carter
(74) *Attorney, Agent, or Firm* — Robert C. Hall

(57) ABSTRACT

Methods for preparing tritium or deuterium labeled thiorphan comprising reacting a compound of formula j wherein m is from 1 to 5 and X is halo, with $Z_2$ wherein Z is tritium or deuterium, in the presence of a catalyst, to form a compound of formula k wherein n is from 1 to 5, provided that n is less than or equal to m.

13 Claims, No Drawings

PROCESS FOR SYNTHESIS OF TRITIATED AND DEUTERATED THIORPHAN AND ACETORPHAN

CROSS REFERENCE TO RELATED APPLICATIONS

This application claims benefit under 35 U.S.C. 119(e) of U.S. Provisional Application No. 61/014,120, filed Dec. 17, 2007 which is hereby incorporated by reference in its entirety.

FIELD OF THE INVENTION

This invention pertains to synthesis of tritiated and deuterated compounds, and more specifically to a method of preparing tritiated or deuterated thiorphan.

BACKGROUND OF THE INVENTION

Thiorphan, or (2-mercaptomethyl-3-phenyl-propionylamino)-acetic acid, is a thiol-containing drug that has been clinically administered as its S-acetyl O-benzyl prodrug racecadotril (also known as acetorphan) for the treatment of diarrhea (Matheson A J, Noble S. *Drugs* 2000; 59: 829-835; Huijghebaert et al., *Dig Dis Sci* 2003; 48: 239-245). Thiorphan shows low-nanomolar inhibitory activity against neutral endopeptidase (NEP or enkephalinase), a zinc-metallopeptidase widely distributed in peripheral tissues and in the brain, whose biological functions include catabolism of the opioid peptides (Rogues et al., *Nature* 1980; 288: 286-288; Lecomte et al., *J Pharmacol Exp Ther* 1986; 237: 937-944).

Enkephalinase inhibitors have received comprehensive studies for their potential therapeutic applications, namely in CNS and digestive tract diseases (Beamont A, Fournie-Zalusk M-C, Rogues B P. In Zinc Metalloproteases in Health and Disease, Hooper N M (ed.) Talor & Francis: London, UK, 1996; 105-129.). Tritium labelled thiorphan (Pollard et al., *Eur J Pharmacol* 1987; 133: 155-164, De la Baume et al., *Eur J Pharmacol* 1988; 149: 121-129) and acetorphan (De la Baume et al., *J Pharmacol Exp Ther* 1988; 247: 653-660) have been used as radioactive probes for characterization of enkephalinase.

Tritium and deuterium labelling of thiorphan is difficult due to the presence of a mercapto functional group, which is troublesome for reactions often used in aromatic tritiation, such as halogenation and catalytic halogen-tritium displacement.

There are two types of tritium labelled thiorphan known in the literature: one with the tritium labelling on the glycine methylene portion (formula 1)

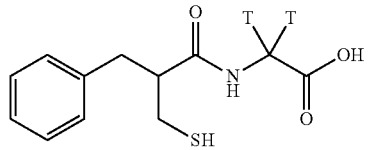

(1)

which is prepared using commercially available [$^3$H]-glycine as tritium source (Pollard et al., *Eur J Pharmacol* 1987; 133: 155-164, De la Baume et al., *Eur J Pharmacol* 1988; 149: 121-129), and the other with tritium labeling on the phenyl ring portion (formula 2)

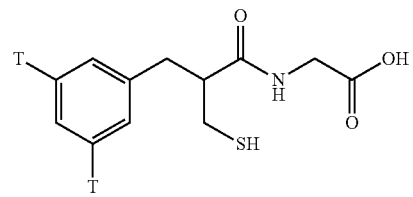

(2)

which is prepared through tritium-halogen exchange reaction via preparation of the corresponding halo-substituted precursor (Fournie-Zaluski et al., *Pept Synth Struct Funct: Proc 7th Am Pept Symposium*, Rich D H, Gross E (ed). Pierce Chem Co: Rockford, Ill., 1981; 425-428). The synthetic yields for both types of tritium-labeled thiorphan are very low, due to either catalyst poisoning by the divalent sulfur group or to lengthy multi-step synthetic procedures. Direct halogenation of thiorphan or acetorphan leads to sulfur oxidation, forming a disulfide during aromatic iodination with bis(pyridine)iodonium tetrafluoroborate, or forming a sulfonic acid upon bromination. These problems have limited the availability and use of [$^3$H]- and [$^2$H]-thiorphan. Therefore, a new and robust synthesis of [$^3$H]- and [$^2$H]-thiorphan is needed.

SUMMARY OF THE INVENTION

The invention provides methods for preparing tritium or deuterium labeled thiorphan and intermediates thereof, the methods comprising:
reacting a compound of formula j

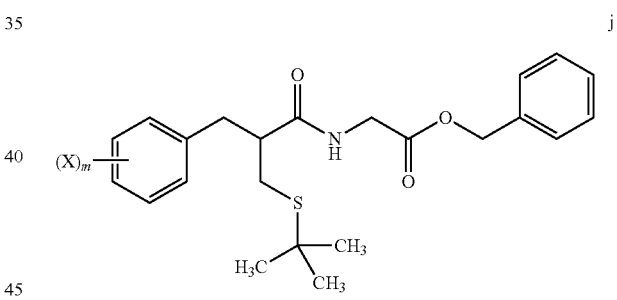

j wherein:
m is from 1 to 5; and
X is halo;
with $Z_2$ wherein Z is tritium or deuterium,
in the presence of a catalyst,
to form a compound of formula k

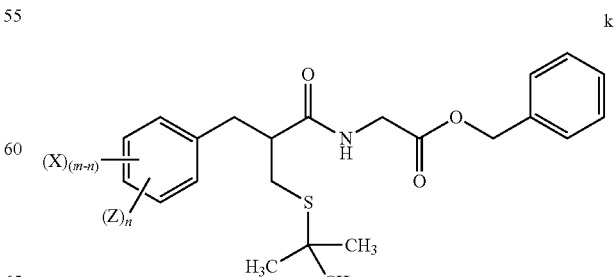

k wherein n is from 1 to 5, provided that n is less than or equal to m.

The method is useful for.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxy-ethyl, 1-(2-methoxyethyl)-3-methoxypropyl, and 1-(2-methoxyethyl)-3-methoxypropyl.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

Heteroarylalkyl" or "heteroaralkyl" means a group of the formula —R—R' wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Polar aprotic solvent" means a solvent comprised of molecules having polar groups thereon, but without mobile protons. Exemplary polar aprotic solvents include, without limitation, dimethyl formamide, acetonitrile, dimethyl sulfoxide, N,N-dimethyl acetamide, N-methylpyrrolidinone, tetrahydrofuran, dioxane, ethyl acetate, tetrahydropyran, pyridine, acetone, 2-propanone, 2-butanone, ethylene glycol dimethyl ether, methylene chloride, chloroform, and the like.

"Thiorphan" means (2-mercaptomethyl-3-phenyl-propionylamino)-acetic acid, including any esters thereof "Thiorphan as used herein thus includes the S-acetyl O-benzyl prodrug of thiorphan, also known as "racecadotril" and "acetorphan".

"Optionally substituted", when used in association with "aryl", phenyl", "heteroaryl" "cycloalkyl", "heterocyclyl", or "aniline" means an aryl, phenyl, heteroaryl, cyclohexyl, heterocyclyl or aniline which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solution" as used herein is meant to encompass liquids wherein a reagent or reactant is present in a solvent in dissolved form (as a solute) or is present in particulate, undissolved form, or both. Thus, in a "solution", it is contemplated that the solute may not be entirely dissolved therein and solid solute may be present in dispersion or slurry form. Accordingly, a "solution" of a particular reagent or reactant is meant to encompasses slurries and dispersions, as well as solutions, of such reagents or reactants. "Solution" and "Slurry" may be used interchangeable herein.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.5. Any open valency appearing on a carbon, oxygen or nitrogen atom in the structures herein indicates the presence of a hydrogen atom. Where a chiral center is present in a structure but no specific stereochemistry is shown, both stereoisomers associated with the chiral center are encompassed by the structure.

Methods

The methods of the invention will be more fully understood by first referring to Scheme A below, wherein m is from 1 to 5, n is from 1 to 5 provided that n is less than or equal to m, X is halo (preferably bromo or iodo), Y is a leaving group and may be the same or different on each occurrence, R is lower alkyl and may be the same or different upon each occurrence, Ar is aryl, and Z is deuterium or tritium.

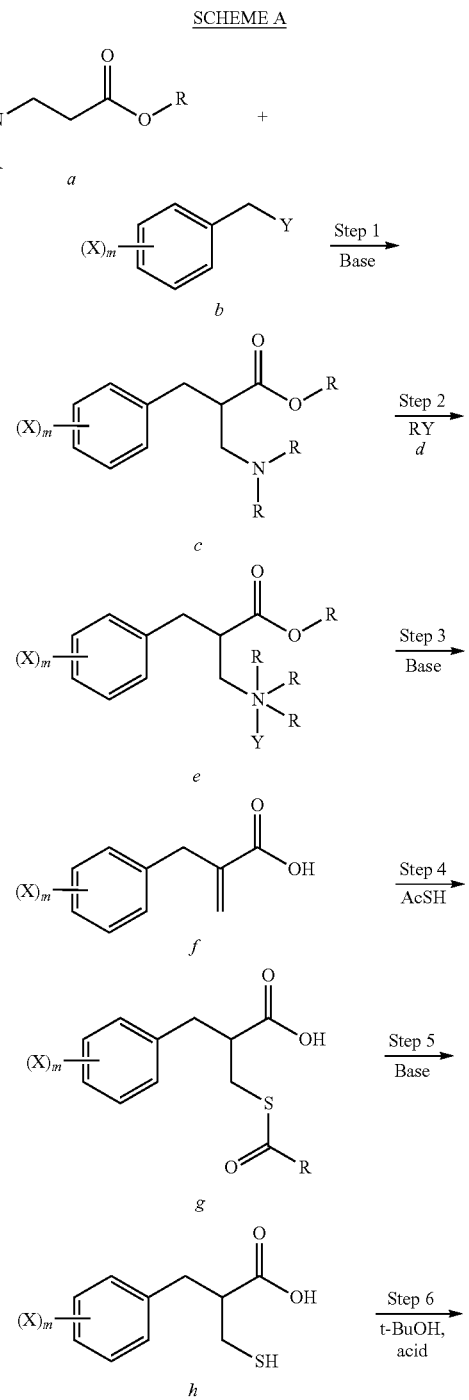

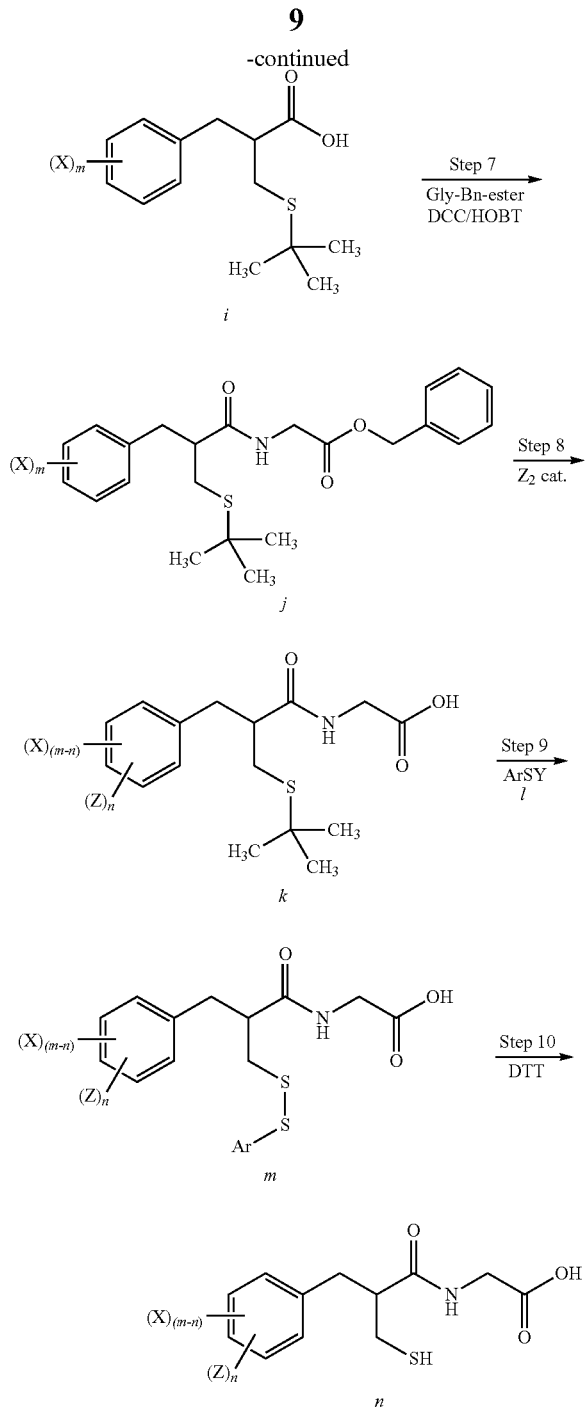

In step 1 of scheme A, an alkylation reaction is carried out by treating amino ester compound a with benzyl compound b in the presence of base and under polar aprotic solvent conditions, to afford benzyl amino ester compound c. The amino ester may be, for example, 3-dimethylamino-propionic acid methyl ester. Benzyl compound b may be, for example, 3-bromo-benzyl bromide, 4-bromo-benzyl bromide, 3,5-di-bromo-benzyl bromide, 3-iodo-benzyl bromide, or the like. A preferred base for this step is lithium diisopropylamide, and a preferred solvent is tetrahydrofuran.

In step 2, an N-alkylation occurs by reaction of benzyl amino ester compound c with alkylating agent d, to afford the quaternized ammonium compound e. The alkylating agent d in many embodiments may be methyl iodide, such that quaternized compound e is an iodide salt. The reaction of step 2 may be carried out under polar protic solvent conditions.

In step 3, quaternized compound e is treated with base to remove the ammonium moiety and provide an unsaturated benzyl compound f. The reaction of step 3 may be carried out using sodium or potassium hydroxide under aqueous solvent conditions. The ester group of compound e is hydrolyzed during this step to provide the corresponding acid.

In step 4 compound f is treated with an acyl thio compound AcSH such as thioacetic acid, to yield thio ester compound g. Polar aprotic solvent conditions may be used in this step. In many embodiments the acyl thio compound itself may be used as a solvent with excess AcSH removed after the reaction.

In step 5, thio ester compound g undergoes hydrolysis to remove the acyl group and provide the corresponding thio compound h. The hydrolysis of step 5 may be carried out, for example, using sodium or potassium hydroxide under aqueous solvent conditions.

An S-alkylation occurs in step 6, wherein thio compound h is reacted with tert-butanol in the presence of acid to afford tert-butyl thioether compound i. The reaction of step 6 may be carried out under aqueous conditions using HCl or like acid. In many embodiments the thio compound g of step 5 does not need to be isolated, but can undergo S-alkylation directly.

In step 7, tert-butyl thioether compound i is treated with glycine benzyl ester to form amide compound j. The amide formation of step 7 may be carried out in the presence of a carbodiimide such as DCC under polar aprotic solvent conditions, and in the presence of an amine base.

Catalytic deuteration or tritiation occurs in step 8, replacing each halo group Z on compound j with a corresponding deuterium or tritium Z, to afford labeled amide compound k. The deuteration or tritiation may be carried out using a platinum or palladium catalyst in the presence of $D_2$ or $T_2$ gas, under aqueous solvent conditions. The benzylic ester of compound i is removed by this step to leave the corresponding acid group. The reaction of step 8 may be carried out under aqueous solvent conditions, preferably in the presence of an amine base such as triethylamine.

In many embodiments complete reductive deuteration or tritiation may be carried out in step 8. In such embodiments m=n such that no residual halo groups X remain on compound k. In other embodiments a partial reduction may be carried out (by reducing the amount of $Z_2$ used) such that one or more halo groups X remain on compound k after deuteration or tritiation. The value of n will always be less than or equal to that of m.

In step 9, labeled amide compound k is treated with aryl sulfenyl compound l to yield labeled disulfide compound m. Aryl sulfenyl compound may comprise, for example, a phenyl sulfenyl halo compound such as a phenyl sulfenyl chloride. Preferably, a nitro activating group is present at the 2- and/or 4-position of the phenyl sulfenyl halide compound. The reaction of step 9 may be carried out under polar, protic solvent conditions in the presence of acid.

In step 10 the disulfide group of compound m is reduced to provide labeled thiorphan compound n in accordance with the invention. The reaction of step 10 may be achieved using dithiothreitol (Cleland's reagent) under polar aprotic solvent conditions, preferably in the presence of an amine base.

Accordingly, the invention provides methods for preparing tritium or deuterium labeled thiorphan, comprising:

reacting a compound of formula j.

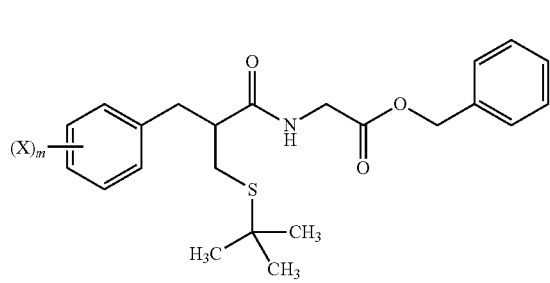

j wherein:
m is from 1 to 5; and
X is halo;
with $Z_2$ wherein Z is tritium or deuterium,
in the presence of a catalyst,
to form a compound of formula k

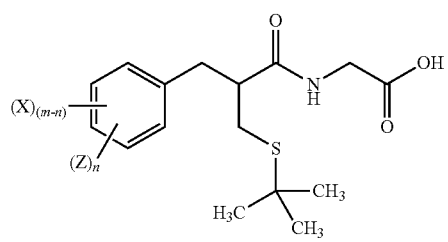

k wherein n is from 1 to 5, provided that n is less than or equal to m.

The methods may further comprise:

reacting the compound of formula k with a reagent of formula l

ArSY      l wherein:
Ar is substituted or unsubstituted phenyl; and
Y is a leaving group;
to form a compound of formula m

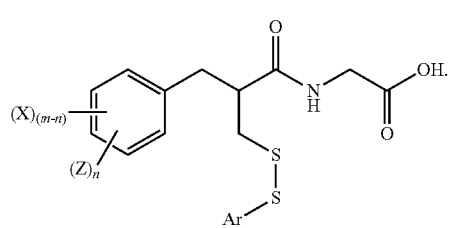

m

The methods may further comprise:
reducing the compound of formula m to form a compound of formula n

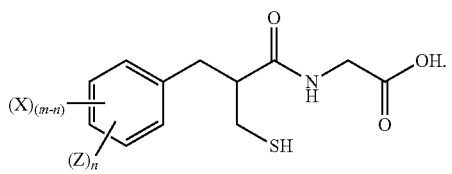

n

The methods may further comprise:
reacting a compound of formula i

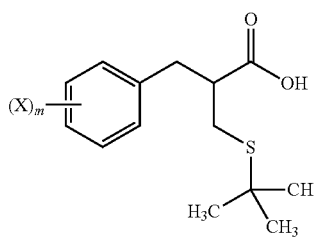

i with glycine benzyl ester, to provide the compound of formula j:

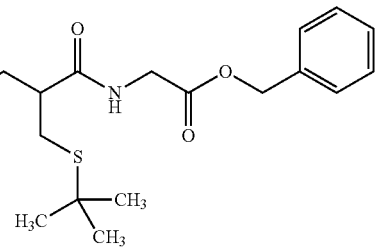

The methods, in certain embodiments, more specifically comprise: reacting a compound of formula h

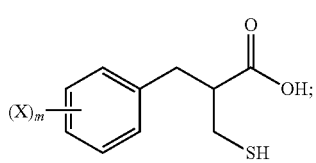

h wherein m and X are as defined herein,
with tert-butanol,
to provide a compound of formula i

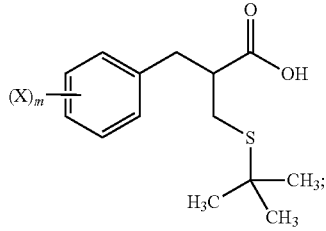

reacting the compound of formula i with glycine benzyl ester, to form a compound of formula j;

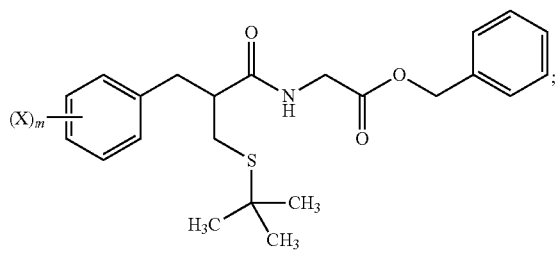

reacting the compound of formula j with $Z_2$ wherein Z is tritium or deuterium, in the presence of a catalyst,
to form a compound of formula k

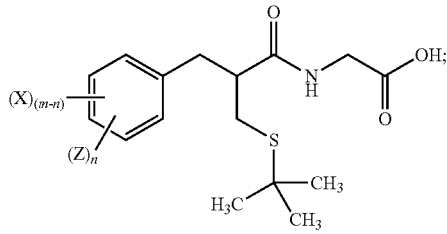

reacting the compound of formula k with a reagent of formula 1

ArSY  1 wherein Ar and Y are as defined herein,
to form a compound of formula m

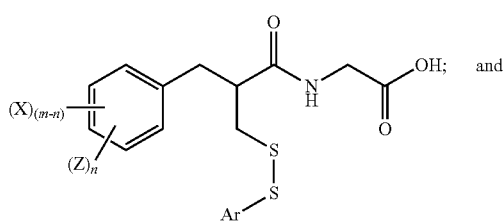

and reducing the compound of formula m to form a compound of formula n

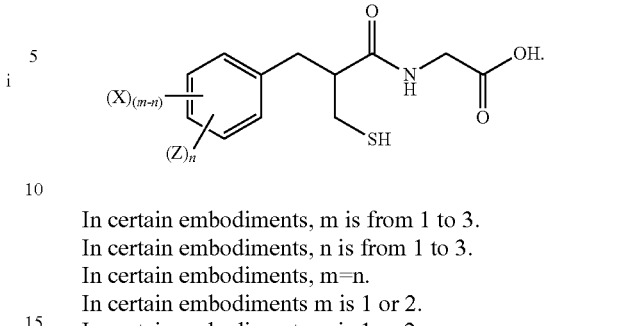

In certain embodiments, m is from 1 to 3.
In certain embodiments, n is from 1 to 3.
In certain embodiments, m=n.
In certain embodiments m is 1 or 2.
In certain embodiments, n is 1 or 2.
In certain embodiments X is bromo or iodo.
In certain embodiments X is bromo.
In certain embodiments X is iodo.
In certain embodiments m is 1 and X is bromo at the 3-position of the phenyl ring.
In certain embodiments m is 1 and X is bromo at the 4-position of the phenyl ring.
In certain embodiments m is 2 and X is bromo at the 3- and 4-positions of the phenyl ring.
In certain embodiments m is 1 and X is iodo at the 3-position of the phenyl ring.
In certain embodiments m is 1 and X is iodo at the 4-position of the phenyl ring.
In certain embodiments m is 2 and X is iodo at the 3- and 4-positions of the phenyl ring.
In certain embodiments Y is halo.
In certain embodiments Y is chloro.
In certain embodiments Ar is phenyl substituted once or twice with nitro.
In certain embodiments the compound 1 is 2-nitrophenyl sulfenyl chloride.
In certain embodiments Z is tritium.
In certain embodiments Z is deuterium.
In certain embodiments m is 1, n is 1, and Z is deuterium at the 3-position of the phenyl ring.
In certain embodiments m is 1, n is 1, and Z is deuterium at the 4-position of the phenyl ring.
In certain embodiments m is 2, n is 2, and Z is deuterium at the 3- and 4-positions of the phenyl ring.
In certain embodiments m is 1, n is 1, and Z is tritium at the 3-position of the phenyl ring.
In certain embodiments m is 1, n is 1, and Z is tritium at the 4-position of the phenyl ring.
In certain embodiments m is 2, n is 2, and Z is tritium at the 3- and 4-positions of the phenyl ring.
In certain embodiments the catalyst used with $Z_2$ is a platinum or palladium catalyst.
In certain embodiments the catalyst used with $Z_2$ is a palladium catalyst on activated carbon.
In certain embodiments the catalyst used with $Z_2$ is Pd(OH)$_2$ on activated carbon.
In certain embodiments the reaction of the compound of formula i with glycine benzyl ester is carried out in the presence of a carbodiimide.
In certain embodiments reduction of the compound of formula m is carried out using dithiothreitol.
The methods of the invention advantageously provide for tritiation or deuteration of a tert-butyl thio compound, which allows isotope labeling in high yield and with good purity. The tert-butyl group is then easily removed from the thio group to provide labeled thiorphan.

Many variations on the above methods are possible within the scope of the invention. Specific details for the methods of the invention are described in the Examples section below.

Utility

The methods and compounds of the invention are useful for preparation of enkephalinase inhibitors and for preparation of radioactive or labeled probes for characterization of enkephalinase.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| AcOH | Acetic acid |
| Bn | Benzyl |
| (BOC)$_2$O | di-tert-Butyl dicarbonate |
| t-BuLi | tert-Butyllithium |
| t-BuOH | tert-Butyl alcohol |
| DCM | Dichloromethane/Methylene chloride |
| DEA | Diethylamine |
| DIPEA | Diisopropylethylamine |
| DIBALH | Diisobutylaluminum hydride |
| DMF | N,N-Dimethylformamide |
| DTT | Dithiothreitol |
| EtOAc | Ethyl acetate |
| HPLC | High pressure liquid chromatography |
| LDA | Lithium diisopropylamine |
| MeOH | Methanol |
| TEA | Triethylamine |
| TFA | Trifluoroacetic acid |
| THF | Tetrahydrofuran |
| TMS | trimethylsilyl |

Proton NMR spectra were recorded on Bruker 300 MHz spectrometers. LC/MS analyses were carried out on a Finnigan LCQ-Advantage ion trap mass spectrometer equipped with an electrospray ionization (ESI) source. Analytic HPLC was run on a Waters 2695 System with a Waters 2699 diode array detector, and preparative HPLC on a Beckman System 32 Karat Gold using a 125 Solvent Module and a 166 detector. Column chromatography was run on a Teledyne Isco Combiflash Companion System with Thompson prepacked E-Merck silica gel cartridges. Thin layer chromatography used Analtech Silica Gel GF 250 micro plates. UV detection was at 220 or 256 nm and radio detection was on an IN/US System β-Ram (HPLC) and a Bioscan System 200 Imaging Scanner (TLC).

Example 1

(2-mercaptomethyl-3-(3-deutero-phenyl)-propionylamino)-acetic acid

The synthetic procedure used in this Example is outlined in Scheme B.

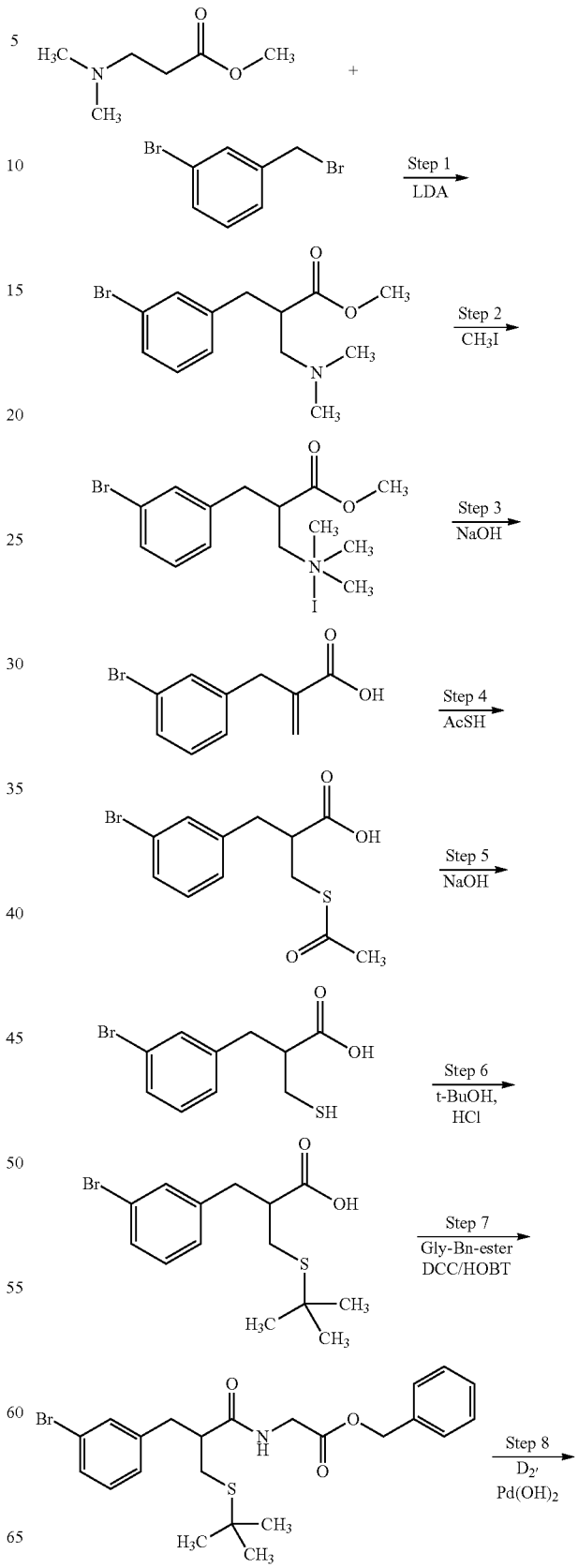

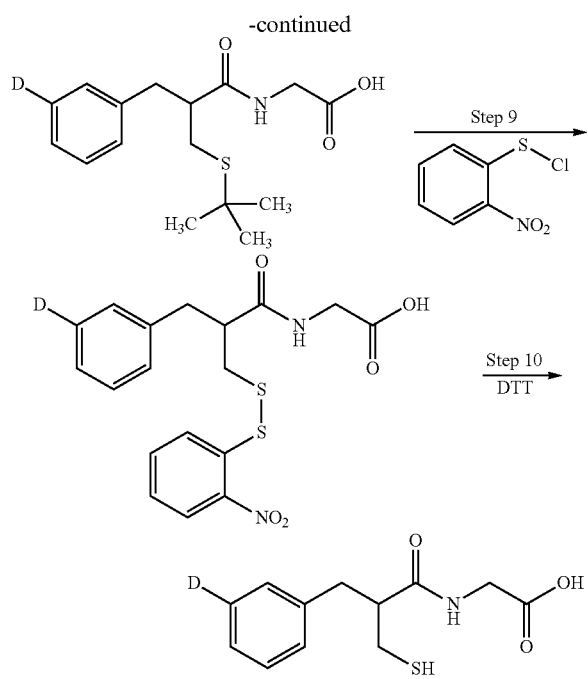

Step 1
3-(3-Bromo-phenyl)-2-dimethylaminomethyl-propionic acid methyl ester To a 100 ml round bottom flask under $N_2$ was added anhydrous THF (20 ml) and lithium diisopropylamide (1.8 M in THF/heptane/ethylbenzene, 4 ml, 7.2 mmol) and the mixture was cooled to −30° C. with a dry ice/MeOH bath. To this, a solution of methyl 3-(dimethylamino)propionate (0.92 g, 7 mmol) in THF (5 ml) was added dropwise; the initial yellowish solution turned into a yellowish suspension. The mixture was aged at −30° C. for 15 min, a solution of 3-bromobenzyl bromide (1.75 g, 7 mmol) in THF (5 ml) was added dropwise causing the suspension to become clear. Stirring continued at −30~−15° C. for 3 h. The mixture was quenched with saturated $NH_4Cl$ solution to pH ~8, and extracted with ether three times. Organic layers were combined, washed with water and dried over sodium sulfate. The crude product was purified by silica gel flask column chromatography eluting with 0 to 5% MeOH in $CH_2Cl_2$ to give the desired 3-bromo as a light yellow oil (0.762 g) in 36% yield. $^1H$ NMR ($CDCl_3$) δ 2.24 (s, 6H), 2.28, 2.65 (2H, m), 2.83 (m, 3H), 3.62 (s, 3H), 7.13 (m, 2H), 7.36 (s, d, 2H); MS (ES+) [M+H+]: 300, 302.

3-(4-Bromo-phenyl)-2-dimethylaminomethyl-propionic acid methyl ester was prepared similarly from 4-bromobenzyl bromide in 32% yield. $^1H$ NMR ($CDCl_3$) δ 2.23 (s, 6H), 2.28, 2.64 (2H, 2m), 2.82 (m, 3H), 3.61 (s, 3H), 7.03 (d, J=8.42 Hz, 2H), 7.39 (d, J=8.42 Hz, 2H); MS (ES+) [M+H+]: 300, 302. As a by-product, N,N-dimethyl-4-bromobenzylamine was isolated in 13% yield. $^1H$ NMR ($CDCl_3$) δ 2.22 (s, 6H), 3.37 (s, 2H), 7.18 (d, J=8.32 Hz, 2H), 7.44 (d, J=8.36 Hz, 2H); MS (CI) [M+H+]: 214, 216.

Step 2 2-(3-Bromobenzyl)-3-methoxy-N,N,N-trimethyl-3-oxo-1-propanaminium iodide To a 10 ml pear-shaped flask containing 3-(3-bromophenyl)-2-dimethylaminomethylpropionic acid methyl ester (0.762 g, 2.54 mmol) were added isopropanol (5 ml) and iodomethane (480 µl, 1.09 g, 7.68 mmol). The mixture was stirred overnight, and the resultant white suspension was filtered and the solid was washed with isopropanol and air-dried to give 2-(3-bromobenzyl)-3-methoxy-N,N,N-trimethyl-3-oxo-1-propanaminium iodide, 0.95 g, 85% yield. 2-(4-Bromobenzyl)-3-methoxy-N,N,N-trimethyl-3-oxo-1-propanaminium iodide was prepared similarly from 3-(4-bromophenyl)-2-dimethylaminomethylpropionic acid methyl ester in 82% yield. MS (ES+) [M−I−]: 314, 316. HPLC purity: 95%.

Step 3 2-(3-Bromobenzyl)acrylic acid

To a 10 ml round bottom flask containing 2-(3-bromobenzyl)-3-methoxy-N,N,N-trimethyl-3-oxo-1-propanaminium iodide (0.95 g, 2.15 mmol) was added 1 N aqueous NaOH (4.3 ml). The mixture was heated at 105° C. for 2 hours, then cooled to room temperature and acidified with 0.5 N HCl to pH ~1. The white precipitate was isolated by filtration, washed with water, and air-dried to give 2-(3-bromobenzyl) acrylic acid 0.44 g, 85% yield, HPLC purity: 93.0%.

2-(4-Bromobenzyl)acrylic acid was prepared similarly from 2-(4-bromobenzyl)-3-methoxy-N,N,N-trimethyl-3-oxo-1-propanaminium iodide in 93% yield. HPLC purity: 94%. $^1H$ NMR ($CDCl_3$) δ 3.58 (s, 2H), 5.61 (s, 1H), 6.38 (s, 1H), 7.08 (d, J=8.27 Hz, 2H), 7.42 (d, J=8.35 Hz, 2H); MS (ES−) [M−H+]: 239, 241; [2M+Na+−2H+]: 501, 503, 505.

Step 4
2-(Acetylsulfanylmethyl)-3-(3-bromophenyl)propionic acid

To a 5 ml pear-shaped flask containing 2-(3-bromobenzyl) acrylic acid (0.44 g, 1.83 mmol) was added thioacetic acid (1 ml, 1.065 g, 13.99 mmol). The mixture was heated at 50° C. for 2.5 hours, after which excess thioacetic acid was removed under reduced pressure. The residue was co-evaporated with toluene twice, then purified via silica gel column chromatography eluting with 0 to 2% MeOH in $CH_2Cl_2$, giving 2-(acetylsulfanylmethyl)-3-(3-bromophenyl)propionic acid as a colorless glue, 0.55 g, 95% yield, HPLC purity: 96.9%.

2-(Acetylsulfanylmethyl)-3-(4-bromophenyl)propionic acid was prepared similarly from 2-(4-bromobenzyl)acrylic acid in 87% yield. $^1H$ NMR ($CDCl_3$) δ 2.35 (s, 3H), 2.98 (m, 5H), 7.07 (d, J=8.30 Hz, 2H), 7.43 (d, J=8.50 Hz, 2H); MS (ES−) [M−$CH_3CO^-$]: 273, 275; [2M+Na+−2H+]: 653, 655, 657.

Step 5
2-Sulfanylmethyl-3-(3-bromophenyl)propionic acid

To a 2-neck 25 ml round bottom flask containing 2-(acetylsulfanylmethyl)-3-(3-bromophenyl)propionic acid (0.25 g, 0.79 mmol) under $N_2$ was added 0.2 N aqueous NaOH (5 ml, 1 mmol). The mixture was stirred at room temperature for 17 hours, after which 1.9 N NaOH, 0.7 ml). After 15 minutes HPLC showed completion of reaction, HPLC purity: 81% (14% disulfide) of 2-sulfanylmethyl-3-(3-bromophenyl)propionic acid, MS (ES−) [M−H+]: 273, 275, which was used in the same round bottom flask for the next step without further purification.

Step 6 2-(S-t-Butylsulfanylmethyl)-3(3-bromophenyl)propionic acid

To the reaction mixture of step 5, under $N_2$ atmosphere, was injected a mixture of t-BuOH (3 ml) and 37% HCl (2.5 ml). The reaction mixture was heated to reflux for 4 hours, then cooled to room temperature and partitioned between water and CH$_2$Cl$_2$. The combined CH$_2$Cl$_2$ phases were washed with brine, dried over sodium sulfate, filtered, and concentrated under reduced pressure. The crude product was purified by silica gel chromatography eluting with 0 to 5% EtOH in CH$_2$Cl$_2$ to give 2-(S-t-butylsulfanylmethyl)-3-(3-bromophenyl)propionic acid as a colorless, viscous oil, 0.133 g, 51%: HPLC purity: 94.5%, MS (ES−) [M−H$^+$]: 329, 331.

Step 7 2-[3-(3-Bromophenyl)-2-(S-t-butylsulfanylmethyl)propionylamino]acetic acid benzyl ester To a 25 ml pear-shaped flask containing 2-(S-t-butylsulfanylmethyl)-3-(3-bromophenyl)propionic acid (0.22 g, 0.665 mmol) and THF (7 ml), at 0° C. were added dropwise a solution of glycine benzyl ester hydrochloride (0.134 g, 0.665 mmol) and a solution of triethylamine (93 µl, 67.3 mg, 0.665 mmol) in CH$_2$Cl$_2$ (7 ml), followed by dropwise additions of a solution of HOBT (0.102 g, 0.665 mmol) in THF (5 ml) and a solution of 1,3-dicyclohexyl carbodiimide (0.164 g, 0.796 mmol) in CH$_2$Cl$_2$ (6 ml). The ice/water cooling bath was removed and the mixture was stirred at room temperature overnight. After concentration under reduced pressure, the residue was partitioned between water and CH$_2$Cl$_2$, and the combined organic layers were washed with brine, dried over sodium sulfate, filtered, and concentrated under reduced pressure. The crude product was purified by silica gel flash column chromatography eluting with 0 to 50% ether in hexane to give 2-[3-(3-bromophenyl)-2-(S-t-butylsulfanylmethyl)propionylamino]acetic acid benzyl ester as a colorless viscous oil, 0.25 g, 79% yield. HPLC purity: 100%. $^1$H NMR (CDCl$_3$) δ 1.29 (s, 9H), 2.51 (m, 1H), 2.64 (m, 1H), 2.85 (m, 3H), 4.02 (m, 2H), 5.16 (s, 2H), 5.95 (m, 1H), 7.12 (m, 2H), 7.35 (m, 7H); MS (ES+) [M+H$^+$]: 478, 480; (ES−) [M−H$^+$]: 476, 478.

Step 8 [$^2$H]- and [$^3$H]—S-t-Butyl thiorphan

To a 10 ml pear-shaped flask containing a magnetic stirrer bar were added 2-[3-(3-bromophenyl)-2-(S-t-butylsulfanylmethyl)propionylamino]acetic acid benzyl ester (2.5 mg, 0.0052 mmol), 20% Pd(OH)$_2$ on activated carbon (7.2 mg), H$_2$O (1 ml), and triethylamine (10 µl). The flask was vacuum-purged and refilled with D$_2$ gas from a balloon (about 10 ml of open space inside the flask was filled up with D$_2$ gas), and the mixture was stirred for 2 hours. The catalyst was removed by filtration and solvent was evaporated under reduced pressure. The residue was analyzed by HPLC which showed a clean and complete conversion. MS of [$^2$H]—S-t-butyl thiorphan (ES+) [M+H$^+$]: 254, 255, 256. The amount of deuterium incorporation was determined by LC/MS as 30% D$_0$, 47% D$_1$, 22% D$_2$, and 3% D$_3$.

Tritiation was performed in a similar manner, using 6 mg of 2-[3-(3-bromophenyl)-2-(S-t-butylsulfanylmethyl)propionylamino]acetic acid benzyl ester, 18 mg of Pd(OH)$_2$/C, 2.5 mL water, and 25 µl triethylamine, with the reaction mixture stirred for 5 hours, to give a total of 219 mCi of crude product [$^3$H]—S-t-butyl thiorphan, which showed radiochemical purity of ~90% (TLC) or 87.4% (HPLC). Analytical HPLC conditions: Zorbax SB-C8, 4.6×150 mm, 5 µm. A: 0.1% TFA in H$_2$O, B: acetonitrile, gradient from 30 to 90% B 0-20 min; hold 90% B 5 min; post time 10 min; flow rate: 1 ml/min; temp. 30° C., radiodetector. Retention time for [$^3$H]—S-t-butyl thiorphan: 8.28 minutes.

Step 9 [$^3$H]—S-(2-Nitrophenylsulfanyl)thiorphan

To a 25 ml pear-shaped flask was added a solution of [$^3$H]—S-t-butyl thiorphan (43.8 mCi) in MeOH (4 ml). Solvent was evaporated and acetic acid (6 ml) was added to the residue, followed by addition of a solution of 2-nitrobenzenesulfenyl chloride (3.0 mg) in acetic acid (3 ml). The mixture was stirred for one hour, and then acetic acid solvent was evaporated under reduced pressure. The residue was used in the next step without further purification. Analytical HPLC conditions: Zorbax SB-C8, 4.6×150 mm, 5 µm. A: 0.1% TFA in H$_2$O, B: acetonitrile, gradient from 30 to 90% B 0-20 min; hold 90% B 5 min; post time 10 min; flow rate: 1 ml/min; temp. 30° C., radiodetector. Retention time for [$^3$H]—S-(2-nitrophenylsulfanyl)thiorphan: 10.20 minutes.

Step 10 [$^3$H]-Thiorphan

To the crude product of step 9 were added CH$_2$Cl$_2$ (4 ml), DTT (2.9 mg) and triethylamine (10 µl). The mixture was stirred under N$_2$ for 50 minutes, and then concentrated to dryness under reduced pressure, and re-dissolved in 200 µl of 0.2% DTT in MeOH/H$_2$O (1:1). The mixture was purified by preparative HPLC to give [$^3$H]-thiorphan in 26.97 mCi of total activity with 99.8% HPLC radiochemical purity and 18.42 Ci/mmol specific activity. The product was stored as 0.2375 mCi/ml aqueous solution containing 10% MeOH and 0.2% DTT. Analytical HPLC conditions: Zorbax SB-C8, 4.6×150 mm, 5 g. A: 0.1% TFA in H$_2$O, B: 0.1% TFA in ACN, gradient from 10 to 90% B 0-20 min; hold 90% B 5 min; post time 10 min; flow rate: 1 ml/min; temp. 30° C., radiodetector. Rentention time for [$^3$H]-thiorphan: 9.16 minutes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for preparing tritium or deuterium labeled compound of formula k, comprising:

reacting a compound of formula j

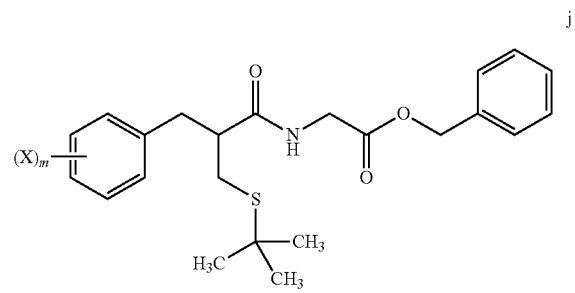

wherein:

m is from 1 to 5; and

X is halo;

with Z$_2$ wherein Z is tritium or deuterium, in the presence of a catalyst, to form a compound of formula k

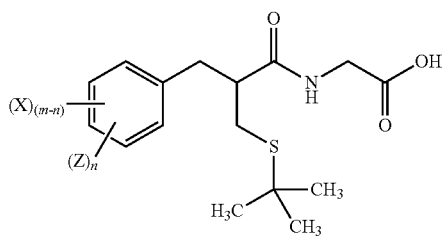

wherein n is from 1 to 5, provided that n is less than or equal to m.

2. The method of claim 1, further comprising:
reacting the compound of formula k with a reagent of formula 1

ArSY     1 wherein:
Ar is substituted or unsubstituted phenyl; and
Y is a leaving group;
to form a compound of formula m

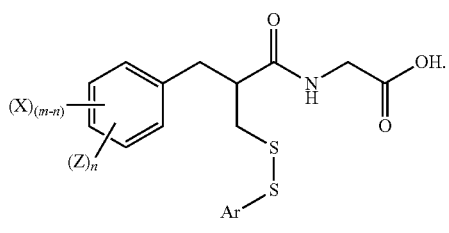

3. The method of claim 2, further comprising:
reducing the compound of formula m to form a compound of formula n

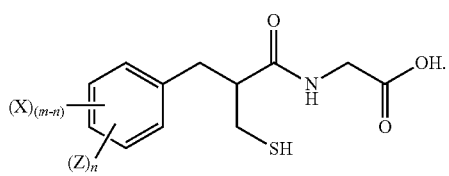

4. The method of claim 1, further comprising:
reacting a compound of formula i

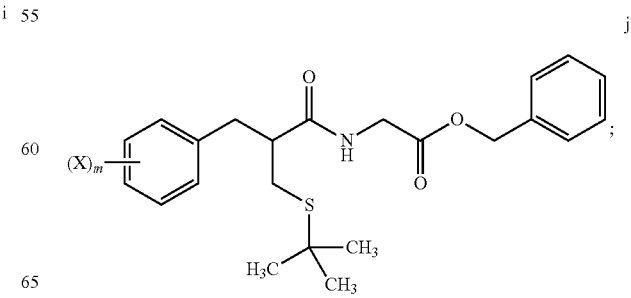

with glycine benzyl ester, to provide the compound of formula j.

5. The method of claim 4, further comprising:
reacting a compound of formula h

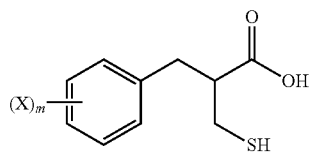

with tert-butanol,
to provide the compound of formula i.

6. A method for preparing labeled thiorphan, the method comprising:
reacting a compound of formula h

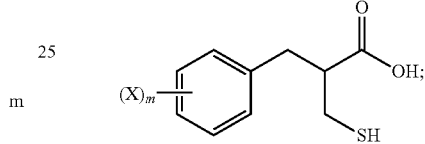

m is from 1 to 5; and
X is halo;
with tert-butanol,
to provide a compound of formula i

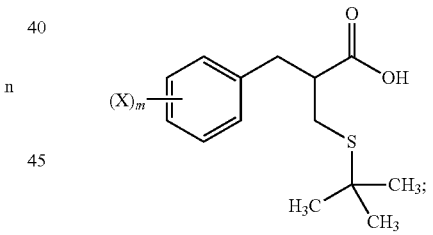

reacting the compound of formula i with glycine benzyl ester, to form a compound of formula j;

reacting the compound of formula j with $Z_2$ wherein Z is tritium or deuterium, in the presence of a catalyst, to form a compound of formula k

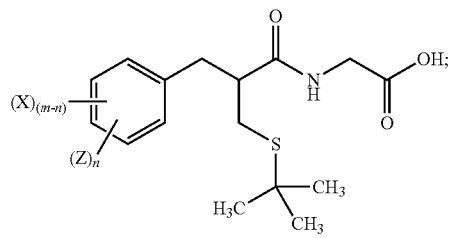

reacting the compound of formula k with a reagent of formula 1

ArSY            1 wherein:
Ar is substituted or unsubstituted phenyl; and
Y is a leaving group;
to form a compound of formula m

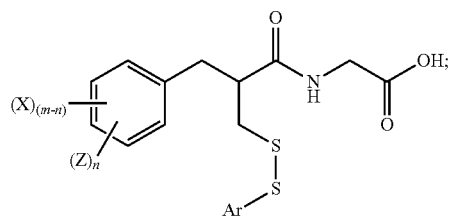

and reducing the compound of formula m to form a compound of formula n

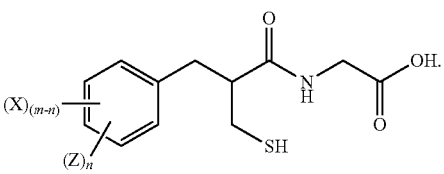

7. The method of claim 1, wherein m is 1 or 2.

8. The method of claim 7, wherein X is bromo or iodo.

9. The method of claim 2, wherein Y is halo.

10. The method of claim 9, wherein Ar is phenyl substituted once or twice with nitro.

11. The method of claim 1, wherein n=m.

12. The method of claim 1, wherein Z=is deuterium.

13. The method of claim 1, wherein Z=is tritium.

* * * * *